United States Patent
Smith et al.

(10) Patent No.: US 9,513,231 B2
(45) Date of Patent: Dec. 6, 2016

(54) TRACKING ENABLED MULTI-AXIS TOOL FOR LIMITED ACCESS INSPECTION

(71) Applicant: The Boeing Company, Chicago, IL (US)

(72) Inventors: Nathan R. Smith, St. Charles, MO (US); James J. Troy, Issaquah, WA (US); Jeffrey R. Kollgaard, Seattle, WA (US); Gary E. Georgeson, Tacoma, WA (US); Paul S. Rutherford, Maple Valley, WA (US)

(73) Assignee: THE BOEING COMPANY, Chicago, IL (US)

( * ) Notice: Subject to any disclaimer, the term of this patent is extended or adjusted under 35 U.S.C. 154(b) by 810 days.

(21) Appl. No.: 13/750,565

(22) Filed: Jan. 25, 2013

(65) Prior Publication Data

US 2014/0210986 A1    Jul. 31, 2014

(51) Int. Cl.
*H04N 7/18* (2006.01)
*G01N 21/954* (2006.01)

(52) U.S. Cl.
CPC .................. *G01N 21/954* (2013.01)

(58) Field of Classification Search
CPC ..... G01N 21/954; G01N 21/956; H04N 7/183
USPC .......... 348/92, 94, 95, 180, 82, 85; 73/866.5
See application file for complete search history.

(56) References Cited

U.S. PATENT DOCUMENTS

| 5,000,533 | A | 3/1991 | Gerwers |
| 5,757,419 | A | 5/1998 | Qureshi et al. |
| 7,114,406 | B2 * | 10/2006 | Wright et al. .............. 73/866.5 |
| 8,109,160 | B2 | 2/2012 | Bossi et al. |
| 2005/0073673 | A1 | 4/2005 | Devitt et al. |
| 2005/0199832 | A1 | 9/2005 | Twerdochlib |
| 2006/0066847 | A1 | 3/2006 | Penza |
| 2009/0180110 | A1 | 7/2009 | Drost et al. |
| 2010/0024559 | A1 | 2/2010 | Bossi et al. |

(Continued)

FOREIGN PATENT DOCUMENTS

| DE | 10 2010 01041 | 9/2011 |
| WO | 2008/034144 | 3/2008 |

OTHER PUBLICATIONS

Machine translation for the description of DE 10 2010 010 419 A1, Sep. 8, 2011.*

(Continued)

*Primary Examiner* — Brian Yenke
*Assistant Examiner* — Jean W Desir
(74) *Attorney, Agent, or Firm* — Thompson Hine LLP

(57) ABSTRACT

A multi-axis tool may include, in some embodiments, a gimbal adapted to be positioned adjacent an opening in a wall; an extended-reach device having first and second ends and an end effector adjacent the first end, the extended-reach device engaging the gimbal for relative rotational movement and relative slidable movement through the opening such that the end effector is positioned on a side of the wall opposite the second end; a sensor system configured to measure a linear position of the extended-reach device relative to the gimbal, and a position and spatial orientation of the end effector relative to the opening; and a computer control connected to receive signals from the sensor system to determine at least one of a position and an orientation of the end effector relative to the opening.

19 Claims, 6 Drawing Sheets

(56) References Cited

U.S. PATENT DOCUMENTS

2012/0147173 A1    6/2012  Lynch

OTHER PUBLICATIONS

EP, Search Report and Opinion, European Application No. 13194549.5, dated May 16, 2014.
Georgeson, G. et al., "Surgical NDE (SuNDE) Tool for Limited Access Inspection," presented at the ASNT Fall Conference, Oct. 24-27, 2011.
Georgeson, G. et al., "Surgical NDE (SuNDE)," AFRL-RX-WP-TR-2011-XXXX, Final Report, Jun. 2011.

* cited by examiner

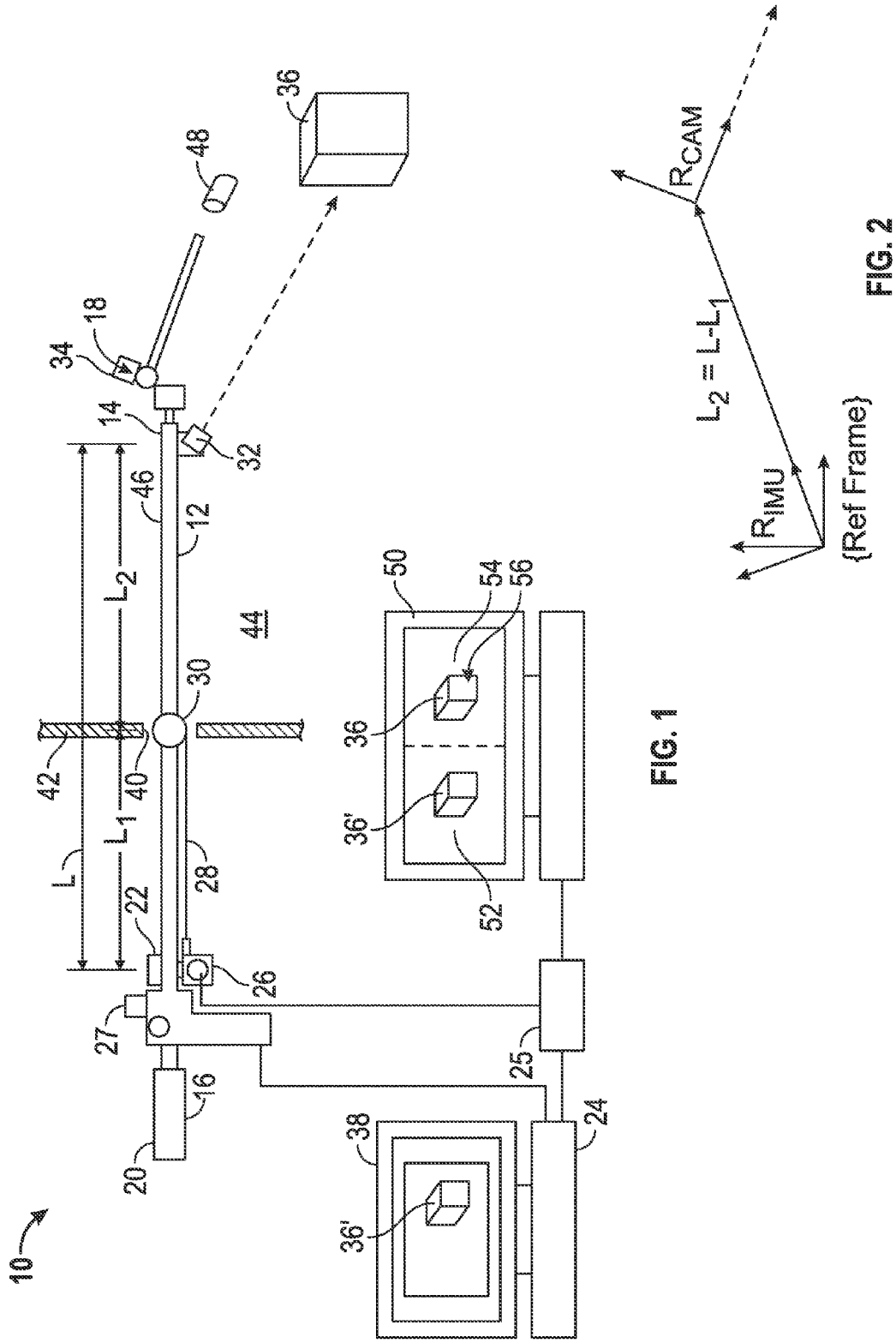

TRACKING ENABLED MULTI-AXIS TOOL FOR LIMITED ACCESS INSPECTION

FIELD

The disclosure relates to systems and methods for nondestructive inspection operated beyond line of sight and in limited access areas, and more particularly, for systems and methods for nondestructive inspection utilizing an instrumented arm equipped with an end effector.

BACKGROUND

Inspection of limited access areas within enclosures, such as aircraft structures, may require disassembly and reassembly of the structure, which is costly and time consuming. As an alternative, such enclosed areas may include an access opening sized to receive a sensor or other instrument that enables a visual inspection. If the interior to be inspected is relatively open, use of such a sensor may be effective. However, in many applications, such an enclosure may include an obstructed interior that may include hardware or other structure that makes access and inspection difficult.

For example, certain internal aircraft structures may require in-service inspection, but such structures may be obstructed by tubes, brackets and actuators that must be removed first. In some cases, initial inspections may take more than 1000 hours, and subsequent inspections may take more than 500 hours. Other internal aircraft components may be obstructed by other structural elements. Because of structural removal issues, an initial aircraft inspection may take more than 2000 hours, and recurring inspections as much as 1100 hours.

Currently, such inspections may be performed using borescopes and remote cameras shaped to be inserted into limited access areas. Such devices may be able to see surface flaws or damage, but not subsurface damage. In many cases, features found using these devices and methods may be misdiagnosed as damage, and only determined to be benign markings after costly disassembly. Fatigue inspections of titanium attach fittings on aircraft may be programmed as visual borescope inspections, but if crack-like indications are found, there is no current method of confirming them other than simply disassembly of the empennage.

Further, with the increase in use of bonded and co-cured composite structures for aircraft, access to the interior for production and in-service inspection may be very difficult, costly, and time-consuming. Such inspection may be so expensive that certain lower-cost structure designs cannot be utilized because of the high cost of performing in-service inspections.

Accordingly, there is a need for a system and method for nondestructive inspection in limited, enclosed areas. There is also a need for a system and method for nondestructive testing that tracks the position and orientation of an inspection device in a confined space.

SUMMARY

In an embodiment, a multi-axis tool that may include a gimbal adapted to be positioned adjacent an opening in a wall; an extended-reach device having first and second ends and an end effector adjacent the first end, the extended-reach device engaging the gimbal for relative rotational movement and relative slidable movement through the opening such that the end effector is positioned on a side of the wall opposite the second end; a sensor system configured to measure a linear position of the extended-reach device relative to the gimbal and a position and spatial orientation of the end effector relative to the opening; and a computer control connected to receive signals from the sensor system to determine at least one of the position and orientation of the end effector relative to the opening.

In another embodiment, a method for inspecting an interior of an enclosure, the enclosure having a wall with an access opening, the method may include providing an extended-reach device having first and second ends and an end effector adjacent the first end; inserting the extended-reach device through the opening such that the end effector is positioned on the side of the wall opposite the second end; detecting with a sensor system a position and spatial orientation of the end effector relative to the opening; and determining a position and orientation of the end effector relative to the opening.

Other objects and advantages of the present disclosure will be apparent from the following description, the accompanying drawings and the appended claims.

BRIEF DESCRIPTION OF THE DRAWINGS

FIG. 1 is a schematic representation of an embodiment of the disclosed tracking-enabled multi-axis tool;

FIG. 2 is a diagram showing the position vectors of the camera and inertial measurement unit of the multi-axis tool of FIG. 1:

DETAILED DESCRIPTION

Figure 3:
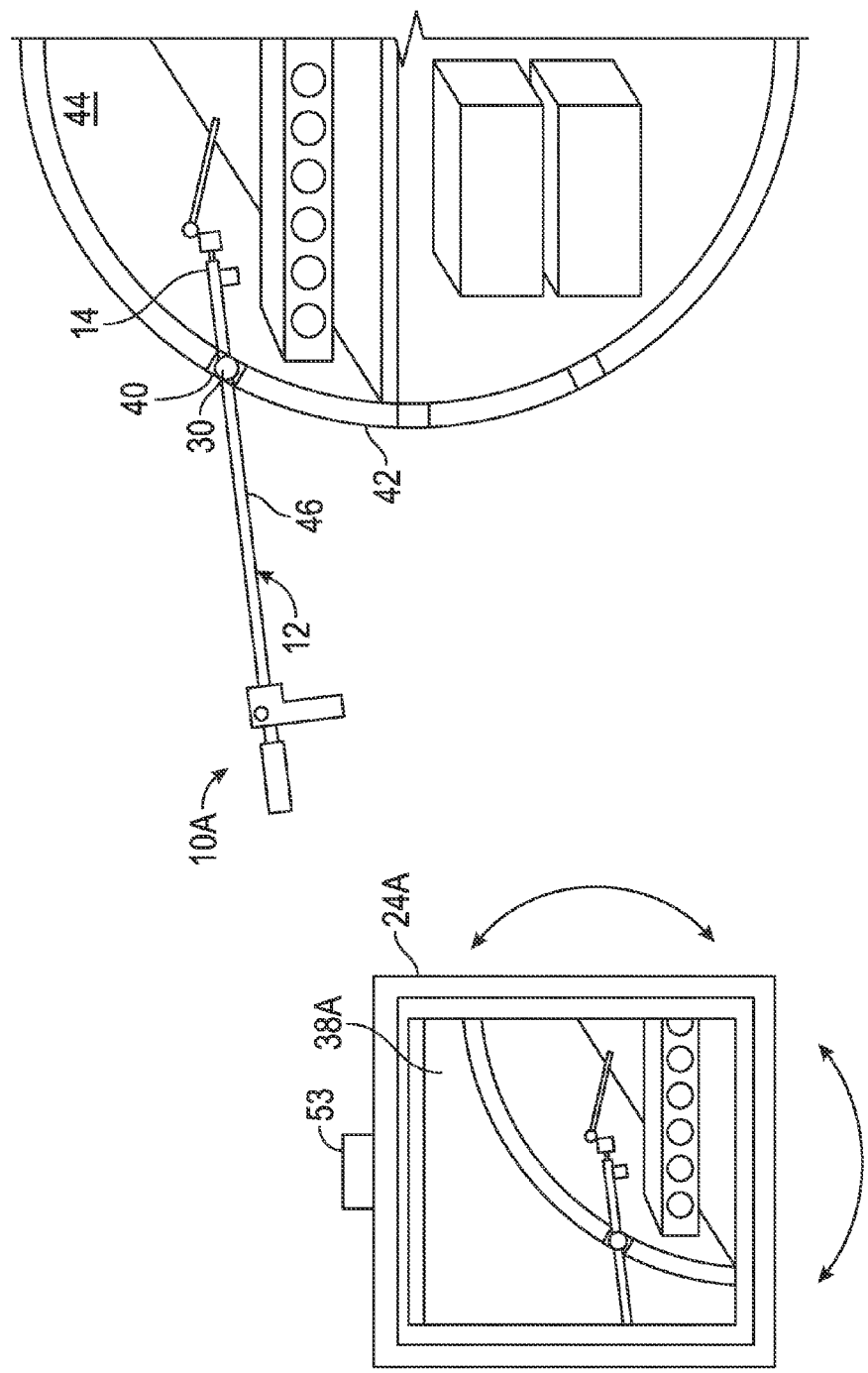
FIG. 3 is another embodiment of the disclosed tracking-enabled multi-axis tool.

As shown in FIG. 1, the disclosed tracking-enabled multi-axis tool, generally designated 10, may include an extended-reach device 12 having a first end 14, and a second end 16. The first end 14 may include an end effector, generally designated 18. The second end 16 may include a handle 20 shaped to be grasped and manipulated by a user (not shown). The extended-reach device 12 may include a sensor system, which in the embodiment of FIG. 1 may include an inertial measurement unit (IMU) 22 that may be connected to a computer control, generally designated 24, that may include an encoder reading device 25.

The sensor system also may include string encoder 26. The string encoder 26 may communicate with the encoder reading device 25 and having a cable 28 attached to a gimbal, which in the embodiment of FIG. 1 may be a slider ball 30 mounted on the extended-reach device 12. Thus, the string encoder 26 may measure the linear position of the extended-reach device 12 relative to the slider ball 30. Optionally, or in addition to string encoder 26, a laser measurement device (LMD) 27 may be mounted on the handle 20 of the extended-reach device 12. As will be described in detail, both string encoder 26 and LMD 27 may be used by computer control 24 to determine the length of the extended-reach device 12 that is beyond the slider ball 30, in order to locate the end of the extended-reach device.

The extended-reach device 12 also may include a camera 32 mounted adjacent the first end 14, and a second laser measurement device (LMD) 34. The camera 32 may be connected to the computer control 24, either by wires or wirelessly, so that an object 36 viewed by the camera may appear on a display 38.

The extended-reach device 12 generally may be elongate in shape and sized such that the first end 14 may be inserted through an access opening 40 in a wall 42 so that the first end 14 may be placed in an enclosed inspection space 44 (see also FIG. 3) on a side of wall 42 opposite the second end 16 and handle 20.

The slider ball 30 may be positioned adjacent the access opening 40, and attached to or otherwise fixed relative to the wall 42. Since the IMU 22 is mounted on the extended-reach device 12, it tracks the orientation of the extended-reach device of the tool 10, which may be equivalent to tracking orientation for any part of the tool that may be rigidly attached to the shaft 46 of the extended-reach device. Signals generated by the IMU 22 indicative of the orientation of the shaft 46 may be received by the computer control 24.

With the embodiment of FIG. 1, the data from IMU 22 may be used to measure orientation of shaft 46. The distance measurement of the shaft relative to the access opening 40 may be acquired from a variety of sources, such as the string encoder 26. Alternately, or in addition, the end effector 14 may utilize the LMD 34 to track the insertion of the end effector device 12 relative to a known inspection location 48.

As shown in FIGS. 1 and 2, with this multi-axis tool 10, the result of data input from the IMU 22, and the string encoder 26 and/or the LMD 34 may be a 4×4 homogenous transformation matrix that encodes the position and orientation of the first end 14 of the shaft 46 of the end-effector 12 relative to a reference coordinate system, designated $R_{IMU}$, shown in FIG. 2. The coordinate system of the camera 32 is designated $R_{CAMERA}$ in FIG. 2. The reference frame of the camera 32, $R_{CAMERA}$, will remain fixed relative to the reference frame of the IMU 22, $R_{IMU}$ because both the IMU and camera are mounted on the shaft 46. Consequently, the orientation of the IMU 22, which may be communicated to the computer control 24, will indicate the orientation of the camera 32.

The distance L from the IMU 22 to the camera 32 (which is a known distance) is expressed as the sum of the distance $L_1$ from the IMU to the slider ball 30, which is indicative of the distance from the IMU to the wall 42, and the distance $L_2$ from the slider ball 30 to the camera 32. Accordingly, the distance from the inspection opening 40 to the object 36 viewed by the camera 32 may be expressed as the difference between the total length L and the length $L_1$ from the IMU 22 to the inspection opening 40. This distance may also be calculated or determined by measuring the distance from the LMD 34 to a known reference object 48 within the interior 44. These measurements may be updated continuously in real time as the extended-reach device 12 is manipulated by an operator (not shown).

In an embodiment, a 3D visualization application may be used to show on display 38 a CAD-based display of the environment in the field of view of the camera 32. The 3D environment may be used to help guide the user and keep track of the inspection sequence. For example, locations of specific areas of interest may be highlighted in one color, while areas that have been inspected, or may still need to be inspected, may be shown in other colors. In addition, a representation of the tool 10 may be shown operating in a virtual environment as well (see, e.g., FIG. 3), since the position and orientation of the tool are known from the tracking instrumentation (IMU 22, string encoder 26, and LMD 34). Accordingly, as shown in FIG. 1, as camera 32 views object 36, the display 38 may show a virtual representation of the object 36' that is generated by the 3D visualization application. If the LMD 34 is utilized, the distance data it provides may be used with the relative orientation of the end effector 18 to create a transformation matrix to post-multiply the transformation of the shaft 46. This provides the location of the laser intersection point with the target object 48, and is computed in the same manner as the relative camera view transformation described above.

The 3D visualization application has an architecture that allows external applications to modify the position and orientation information for the virtual camera or other objects in the 3D environment. In some applications this may be accomplished using a plug-in framework that has an application programming interface (API) to allow control of the visualization environment from a separate application.

In an embodiment, the tool 10 may include a display 50, that may be used in addition to or instead of display 38. This display 50 may show a virtual image 52 of the object 36' alongside an actual camera image 54 of the object 36. This side-by-side display may enable a user to compare the actual object 36 with the virtual object 36', which may enable the operator to detect a defect 56 or other problem with the viewed object. Data and images of the objects 36, 48, as well as the contours and other objects in the inspection space 44 that may enable the 3D visualization application to display virtual images 36' that move as the camera 32 moves with movement of the extended-reach device 12, may be stored in a database that may be part of computer control 24, or may be accessed by computer control from a remote location (not shown).

As shown in FIG. 3, in another embodiment, which may or may not be used in combination with the embodiment shown in FIG. 1, a portable display device 24A, such as a tablet PC (shown), a smartphone, DisplayLink monitor, a wearable, a hand-held device, or a heads-up display, may be equipped with a separate IMU 53 and used to provide virtual viewpoint orientation control. The virtual viewpoint position may be linked to the fixed location of the access port 40, or any location associated with the tool 10A, for example, the first end 14 of the tool. Consequently, any rotation, pivoting or angling of the display device 24A and IMU 53 will result in a corresponding rotation, pivoting or angling of the virtual image 38A. This capability may allow for a more intuitive interface and provide improved situational awareness for the user. If the display device 24A is equipped with a touch-screen display 38A, objects may selected on the screen and positions recorded for further analysis.

Figure 4A:
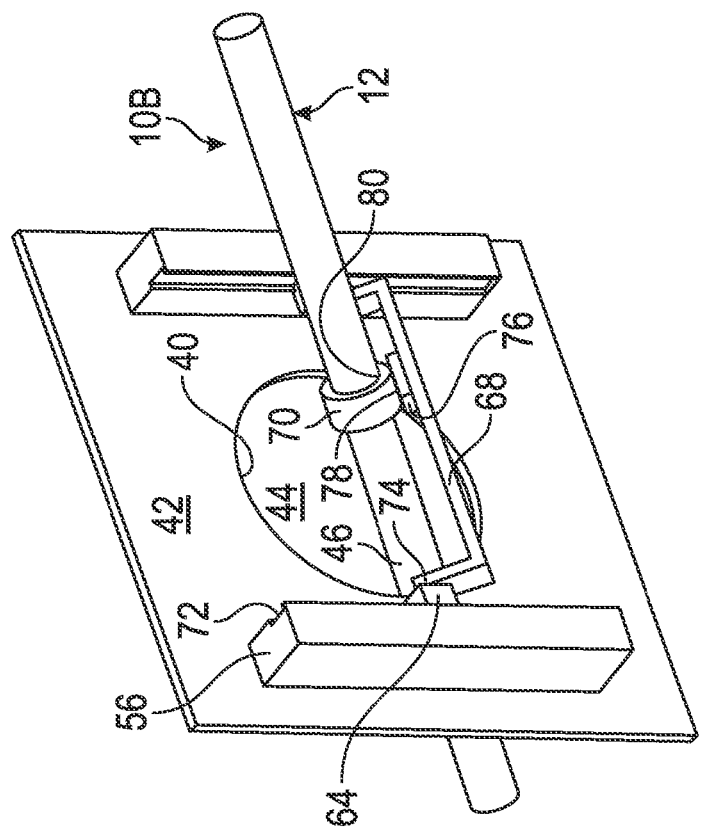
FIGS. 4A and 4B are details of a third embodiment of the disclosed tracking-enabled multi-axis tool.
Figure 4B:
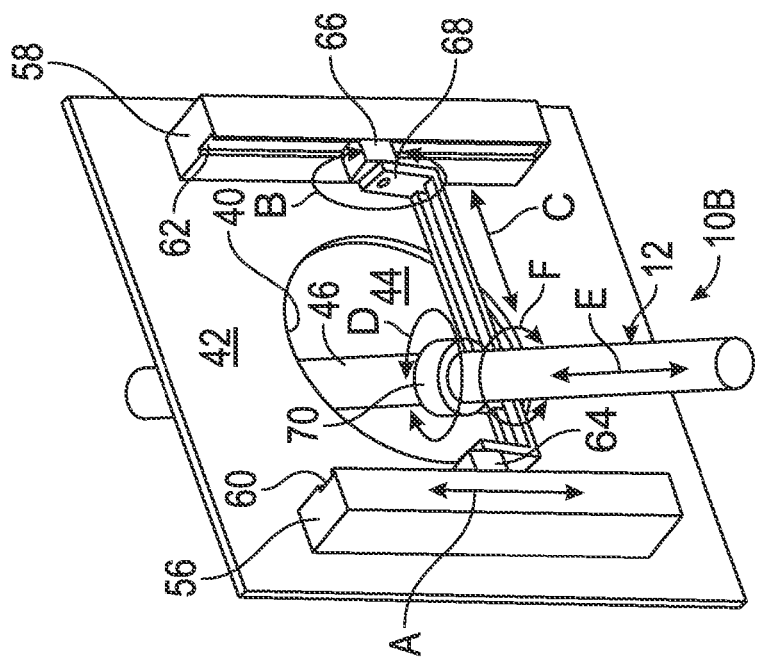

Another embodiment of the multi-axis tool 10B is shown in FIGS. 4A and 4B. With this embodiment, the sensor system, which in the embodiment of FIG. 1 included IMU 22 and slider ball 30, may be replaced or augmented by a system of linear and rotational encoders used to track movements of the extended-reach device 12. The multi-axis tool 10B may include a gimbal that includes parallel slides 56, 58, blocks 64, 66, rail 68, and sliding attachment ring 70 positioned adjacent the opening 40 in the wall 42.

Parallel slides 56, 58 may extend in length and may be attached to the wall 42 by means such as clamps, suction cups, screws and the like (not shown) on either side of inspection opening 40. Slides 56, 58 may include longitudinal slots 60, 62, respectively, that receive blocks 64, 66 for relative slidable movement in the direction of arrow A. The rail 68 may be attached to the blocks 64, 66 for relative rotational movement in the direction of arrow B. The rail 68 may extend between the slides 56, 58 across inspection opening 40. The sliding attachment ring 70 may be mounted on the rail 68 for relative slidable or translational movement in the direction of arrow C, and be mounted for pivotal movement in the direction of arrow D (i.e., about an axis normal to the rail 68) on the rail. Further, the shaft 46 of extended-reach device 12 may engage the sliding attachment ring 70 for relative slidable movement in the direction of arrow E, and relative rotational movement in the direction of arrow F.

As shown in FIG. 4B, rail 56 may include a linear encoder located at 72 to transmit a signal indicative of the position of block 64 relative to rail 56 in the direction of arrow A (FIG. 4A), and block 64 may include a rotational encoder located at 74 that may transmit a signal indicative of the relative rotation angle of slide 68 to block 64 in the direction of arrow B (FIG. 4A). Slide 68 may include a linear encoder located at 76 that may transmit a signal indicative of the position of sliding attachment ring 70 relative to the rail 68 in the direction of arrow C (FIG. 4A), and sliding attachment ring 70 may include rotational encoders located at 78, 80 for transmitting signals indicative of a pivotal orientation of the sliding attachment ring 70 in the direction of arrow D (FIG. 4A) and the rotational position of the shaft 46 in the direction of arrow F (FIG. 4A), respectively. The signals from the encoders 72, 74, 76, 78, 80 all may be transmitted to the computer control 24 (FIG. 1) to give an indication of the orientation of the end effect tool 18 relative to the opening 40. These signals may be processed by the computer control 24 to generate a virtual and/or actual image 52, 54, respectively, of the object 36 being viewed. The embodiment of FIGS. 4A and 4B may eliminate the need for IMU 22. However, string encoder 26 or LDM 34 still may be necessary to detect the "in-and-out" motion of the shaft 46 of the extended-reach device 12 relative to the inspection opening 40 in the direction of arrow E (FIG. 4A).

Figure 5A:
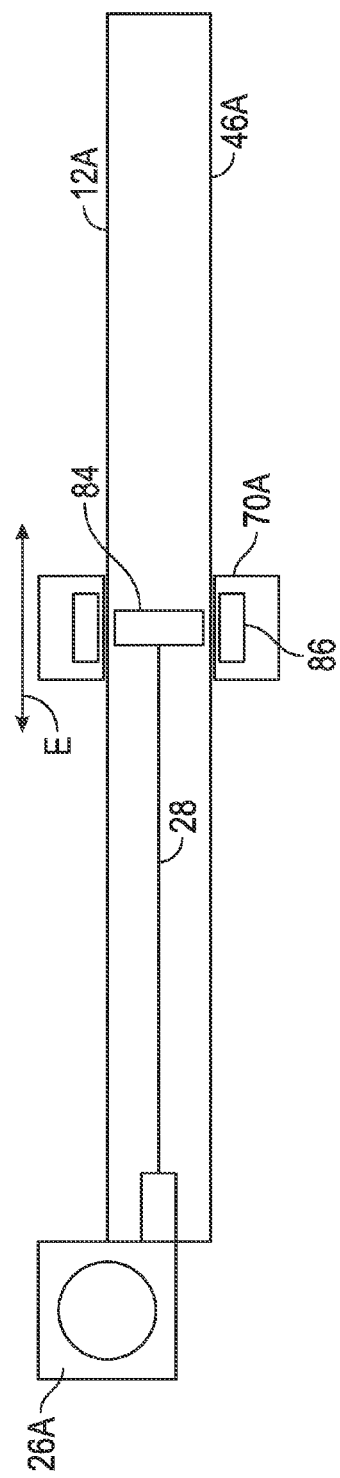
FIGS. 5A, 5B and 5C are schematic representations of different embodiments of the extended-reach device of the disclosed tracking-enabled multi-axis tool.
Figure 5B:
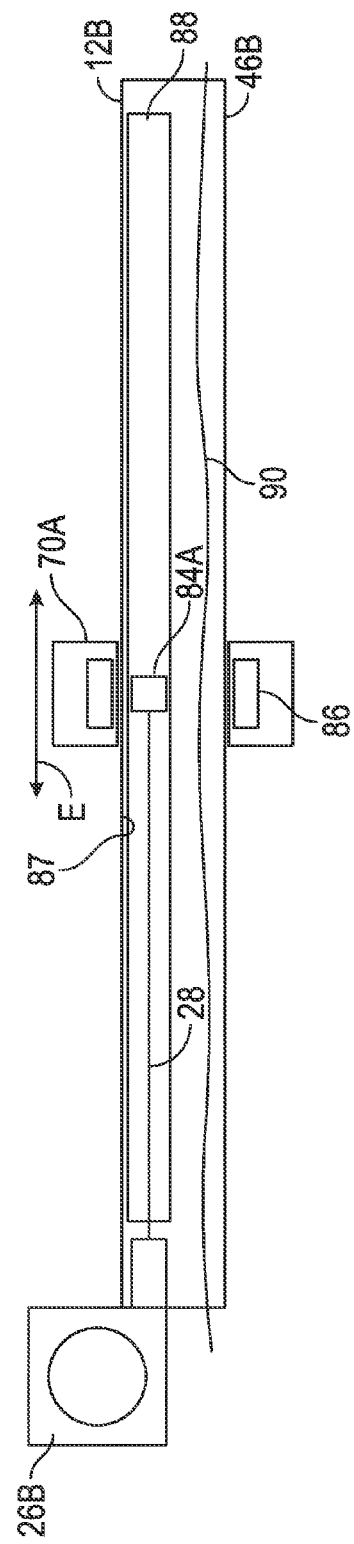
Figure 5C:
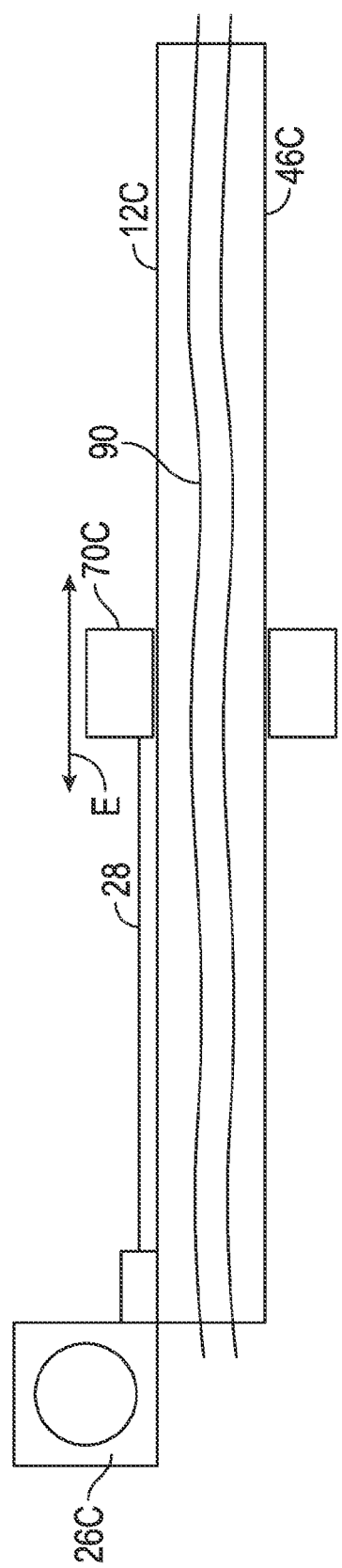

FIGS. 5A, 5B and 5C show different embodiments of the string encoder 26A, 26B, 26C, and sliding attachment ring 70A and 70C that may be used, for example, in the embodiment of FIGS. 4A and 4B to detect motion of the shaft of the extended-reach device 12 in the direction of arrow E (FIG. 4A). As shown in FIG. 5A, string encoder 26A may include a cable 28 that is attached to a disk 84 that may be of ferromagnetic material, such as steel. The disk 84 may be shaped to be positioned within the hollow interior of the shaft 46A for relative slidable movement. The sliding attachment ring 78 may include a ring magnet 86. The ring magnet may act to maintain the metal disk 84 in the position shown in FIG. 5A, namely at or near the center of the sliding attachment ring 70A. As the shaft 46A of the extended-reach device 12A is moved longitudinally (i.e., in the direction of arrow E in FIG. 5A) relative to the sliding attachment ring 70A, the metal disk 84 will remain fixed, aligned with the magnet 86 within the sliding attachment ring, causing the cable 28 either to be withdrawn within the string encoder 26A or extended outwardly from it, thus enabling the string encoder 26A to generate a signal indicative of the relative longitudinal position of the shaft 46A to the sliding attachment ring 70A. In an alternate embodiment of FIG. 5A, the sliding attachment ring 70A may include a metal ring 86, and the disk 84 may be made of a ferromagnetic material. With either embodiment, the magnetic attraction between the disk 84 and the ring 86 may maintain the disk in the position shown in FIG. 5A.

As shown in FIG. 5B, the shaft 46B of the extended-reach device 12A may include a hollow interior that receives a tube 88 that is also hollow, and receives a ring magnet or ferromagnetic disk 84A within it. The tube 88 may be attached to an interior wall 87 of the shaft 46B by an adhesive, bonding or other means. The sliding attachment ring 70A may include a magnet or metal disk (if the disk 84A is comprised of magnetic material) 86. The magnetic attraction between the ring magnet or disk 84A and ring 86 may maintain the magnet or disk 84A in the position shown in FIG. 5B as the shaft 46B is moved longitudinally in the direction of arrow E shown in FIG. 5B relative to sliding attachment ring 70A. Again, this relative movement may cause the cable 28 either to be drawn into the string encoder 26B or extended from it, thus generating a signal indicative of the relative longitudinal position of the shaft 46B to sliding attachment ring 70A. An advantage of including the hollow tube 88 within the interior of shaft 46B is that clearance may be provided for other wires and cable 90 to extend along the interior. Such wires and cables 90 may include connections to the LMD 34 and/or camera 22 (FIG. 1).

As shown in FIG. 5C, the shaft 46C has a hollow interior that provides a conduit for other wires and cables, generally designated 90, to extend through it. The sliding attachment ring 70C itself may be connected by the cable 28 to the string encoder 26C. Relative longitudinal movement of the shaft 46C of the extended-reach device 12C in the direction of arrow E may cause the cable 28 to be withdrawn into or extended outwardly from the string encoder 26C, thereby indicating the relative position of the shaft 46C to the sliding attachment ring 70C.

Figure 6:
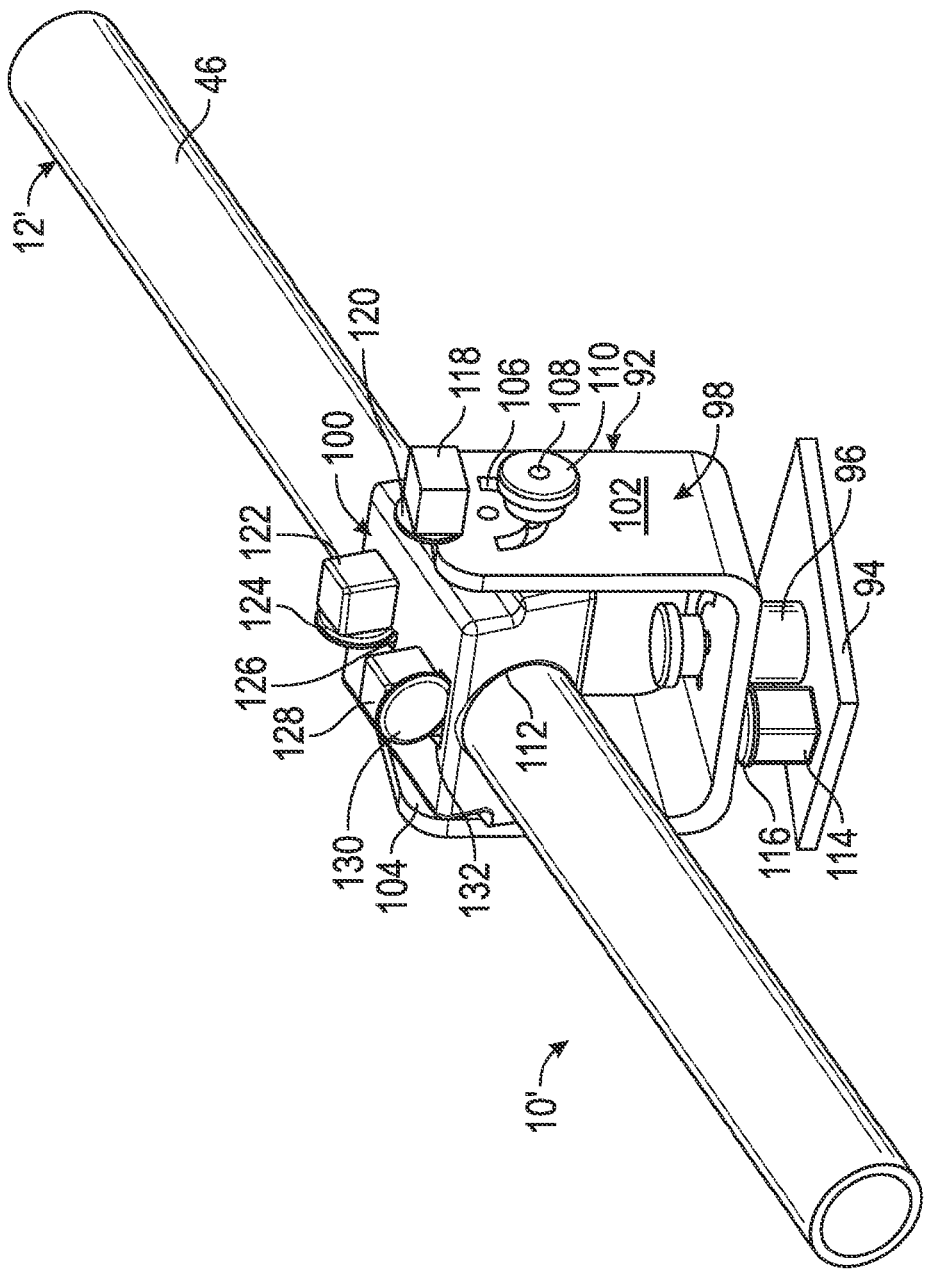
FIG. 6 is yet another embodiment of the disclosed tracking-enabled multi-axis tool.

In yet another embodiment, shown in FIG. 6, the tracking-enabled multi-axis tool, generally designated 10', may include a gimbal in the form of a tilt-swivel support system 92 in place of, for example, the IMU 22, encoder 26 and slider ball 30 components of the embodiment of FIG. 1. Tilt-swivel 92 may include a support 94 that may include a stand (not shown) or an attachment (not shown) to wall 42 (FIG. 1). A shaft 96 is pivotally mounted on support 94 and includes a U-shaped bracket 98 so that the shaft and U-shaped bracket swivel relative to the support 94 about a vertical axis as shown in FIG. 6. A block 100 is shaped to fit between and may be pivotally attached to the arms 102, 104 of the U-shaped bracket 98. Arm 102 may include an arcuate slot 106 that receives threaded stud 108 on which a locking knob 110 is mounted to provide an adjustable friction resistance to pivotal movement of the block 100 relative to the bracket 98.

The block 100 may include a bore 112 shaped to slidably and rotationally receive the shaft 46 of the extended-reach device 12'. A wheel encoder 114 may be mounted on the support 94 and include a wheel 116 that engages shaft 96. Wheel 116 may be oriented to rotate in response to rotation of the shaft 96, and thus encoder 114 may detect swivel movement of U-shaped bracket 98, and thus swivel movement of shaft 46. A wheel encoder 118 may be mounted on arm 112 and include wheel 120 positioned to engage the block 100. Wheel 120 is oriented to rotate in response to pivotal movement of the block, and thus elevational movement of the shaft 46, as it pivots relative to the bracket 98.

A wheel encoder 122 may be mounted on block 100 and include a wheel 124 that extends through a slot 126 in the block to contact shaft 46. Wheel 124 is oriented such that it is rotated in response to longitudinal movement of shaft 46 relative to block 100, and therefore to system 92. A wheel encoder 128 may be mounted on block 100 and include a wheel 130 that extends through slot 132 in block 100 to engage shaft 46. Wheel 130 is oriented such that it rotated in response to rotational movement of the shaft 46 relative to block 100, so that encoder 128 may detect rotational movement of shaft relative to system 92.

Since wheels 124 and 130 are mounted so that they measure different motions (translation and rotation, respectively) of shaft 46, wheels 124 and 130 may be omni wheels that allow the surface on which they are rolling to slide freely in the direction perpendicular to their respective rotation directions.

Encoders 114, 118, 122, and 128 each may be connected to send a signal to computer control 24 (FIG. 1). Consequently, computer control 24 may receive signals indicative of a location of distil end 14 of shaft 46 by calculating the longitudinal, rotational, tilting and swivel movements of the shaft as measured by encoders 114, 118, 122, and 128.

In operation, a user may input to the computer control 24 identification information pertaining to the aircraft or other enclosure to be inspected, and may input identification indicia of the inspection opening 40. This information may enable the computer control to access the appropriate library of data for the enclosure to be inspected. With the embodiment of FIG. 1, the user may attach the slider ball in position at or near the inspection opening 40. With the embodiment of FIGS. 4A and 4B, the user may attach the slides 56, 58 adjacent to the inspection opening 40. At this point, the user may be positioned on the outside of wall 42 and will not be able to see through the inspection opening 40.

The user (or an assistant) then may manipulate the extended-reach device 12 by grabbing the handle 20, such that the distil end 14 of the shaft 46 passes through the inspection opening 40 and enters the inspection space 44. The user may view an actual or virtual image on display 38 or 50 of the inspection space 44. The user may manipulate the extended-reach device 12 so that the camera 32 is oriented to view a desired object 36. With the embodiment of FIG. 1, signals from the IMU 22 and one or both the string encoder 26 and LMD 34 may be utilized by the computer control 24 to determine the location and orientation of the end effector 18 relative to the inspection opening 40. With the embodiment of FIGS. 4A and 4B, the computer control may receive signals from the encoders 72, 74, 76, 78, 80, and string encoder 26 to determine the location and orientation of the end effector 18 relative to the inspection opening 40. Thus, the computer control 24 may display the appropriate virtual image 36' at the appropriate orientation relative to the extended-reach device 12.

If the object 36 includes a defect 56, the defect may appear on the image 54. The user may actuate the computer control 24 (which may be by touching a touch screen display) to make a note of the location of the defect 56, and may actuate the computer control to record the image 54 showing the object 36 and defect 56. Once the inspection is completed, the computer control may generate a report of the image and/or location of the object 36 and defect 56. The inspection may be facilitated by use of the portable device 24A. The portable device may receive information relating to the relevant aircraft and location of the inspection opening 40, and access stored information (either locally on the device 24A or remotely), and display an image 38A of the objects being inspected (FIG. 3). This image may be manipulated by manipulating the spatial orientation of the device 24A to enable a user to visualize the inspection space 44 and the position of the extended-reach device 12 within it.

The foregoing embodiments each provide a multi-axis tool that has the ability to track the position and orientation of the end effector on an extension arm that operates in a confined space. Further, the embodiments enable a user to visualize a virtual representation of the environment being inspected from the perspective of the end effector. This may allow an operator of the tool to have a better situational awareness of the inspection volume. In that environment, a user may view, in certain embodiments, 3D models of all the aircraft components (or other components being inspected) in the inspection region, as well as visualize the inspection tool and even a representation of the view region (frustum) of the video camera on the end effector.

This type of interaction with the physical environment of the objects being viewed with virtual representations of the same physical objects may be facilitated by the ability to track position and orientation of the end effector when registered with the coordinate system of the target object. Objects, in some embodiments, may be highlighted in one color to show a user which items need to be scanned, and in another color to show those items that already have been scanned. In other embodiments, additional information about the objects and environment may be displayed in a properly registered 3D context. In still other embodiments, the computer control 24 may generate reports of the scanning session in which 3D data points are recorded by the control as a way to confirm that required areas have been scanned.

The forms of apparatus and methods described herein are not exclusive of the inventions covered by this disclosure, and variations may be made therein without departing from the scope of the invention.

What is claimed is:

1. A multi-axis tool comprising:
   a gimbal adapted to be positioned adjacent an opening in a wall;
   an extended-reach device having first and second ends and an end effector adjacent the first end, the extended-reach device engaging the gimbal for relative rotational movement and relative slidable movement through the opening such that the end effector is positioned on a side of the wall opposite the second end;
   a sensor system configured to measure a linear position of the extended-reach device relative to the gimbal, and a position and spatial orientation of the end effector relative to the opening; and
   a computer control connected to receive signals from the sensor system to determine at least one of a position and an orientation of the end effector relative to the opening.

2. The multi-axis tool of claim 1, wherein the sensor system includes an inertial measurement unit mounted on the extended-reach device; and at least one of a laser measurement device, a string encoder and a wheeled encoder to track insertion of the extended-reach device into said opening.

3. The multi-axis tool of claim 1, further comprising:
   a slide adapted to be positioned adjacent an opening in a wall;
   the gimbal includes
      a rail attached to the slide and capable of slidable and rotational movement relative to the slide, and
      a sliding attachment ring being attached to the rail for pivotal and translational movement relative thereto; and
   the sensor system being configured to detect a longitudinal position of the rail along the slide, a rotational position of the rail relative to the slide, a position of the sliding attachment ring along the rail, a pivot position of the sliding attachment ring relative to the rail, and a rotational position of the extended-reach device relative to the gimbal.

4. The tool of claim 3, wherein the sensor system includes one or more of a first encoder configured to measure the longitudinal position of the rail along the slide, a second encoder configured to measure the rotational position of the rail relative to the slide, a third encoder configured to measure the position of the sliding attachment ring along the rail, a fourth encoder configured to measure the position of the pivot position of the sliding attachment ring relative to the rail, a fifth encoder configured to measure the linear position of the extended-reach device relative to the sliding attachment ring, and a sixth encoder configured to measure the rotational position of the extended-reach device relative to the sliding attachment ring.

5. The tool of claim 1, wherein the end effector communicates with and is controlled by the computer control.

6. The tool of claim 1, wherein the end effector includes a camera, and the signals received by the computer control are used by the computer control to determine a location and orientation of the camera.

7. The tool of claim 6, wherein the computer control includes a display connected to the camera to show an image transmitted by the camera.

8. The tool of claim 7, wherein the computer control includes a database containing stored images of objects viewed by the camera; and the display is configured to show a stored image of one of the objects adjacent an actual image of the one of the objects viewed by the camera.

9. The tool of claim 6, wherein the computer control includes a hand-held display having an inertial measurement unit; and a database containing stored information pertaining to an interior of an enclosure to be viewed by the camera; the computer control being configured to display a virtual image on the hand-held display of the interior that moves as the hand-held display is oriented by a user.

10. The tool of claim 1, wherein the extended-reach device is a tube.

11. The tool of claim 10, wherein a second one of the ends includes a handle adapted to be grasped by a user.

12. The tool of claim 1, wherein the sensor system includes a string encoder attached to the extended-reach device to transmit the linear position of the extended-reach device relative to the sliding attachment ring.

13. The tool of claim 12, wherein the string encoder includes a first magnet within at least one of the sliding attachment ring and the extended-reach device; and one of a second magnet and a ferromagnetic element within the other of the sliding attachment ring and the extended-reach device; the first encoder including a cable attached to the one of the second magnet and the ferromagnetic element.

14. The tool of claim 13, wherein the cable extends through one of an interior of the extended-reach device and a hollow conduit extending longitudinally through an interior of the extended-reach device, the hollow conduit being shaped to provide clearance within the extended-reach device sufficient to allow wires to extend therethrough; and the one of the second magnet and the ferromagnetic element is located within one of the interior of the extended-reach device and the hollow conduit.

15. A method for inspecting an interior of an enclosure, the enclosure having a wall with an access opening, the method comprising:
  inserting an extended-reach device, the extended-reach device having first and second ends and an end effector adjacent the first end, through the access opening such that the end effector is positioned on a side of the wall opposite the second end;
  detecting with a sensor system, the sensor system having a gimbal adapted to be positioned adjacent the access opening, the extended-reach device engaging the gimbal for relative rotational movement, relative pivotal movement, and relative slidable movement through the access opening, a position and spatial orientation of the end effector relative to the opening; and
  determining a position of the end effector relative to the opening.

16. The method of claim 15, wherein detecting with a sensor system includes providing a slide adapted to be positioned adjacent an opening in a wall; and the gimbal being attached to the slide for linear movement relative thereto.

17. The method of claim 16, wherein the gimbal includes a sliding attachment ring that receives the extended-reach device; and detecting with a sensor system includes detecting a linear position of the extended-reach device relative to the sliding attachment ring.

18. The method of claim 17, wherein the gimbal includes a rail pivotally and slidably attached to the slide, and pivotally and slidably attached to the sliding attachment ring; and detecting with a sensor system includes detecting one or more of a position of the rail along the slide, a rotational position of the rail relative to the slide, a position of the sliding attachment ring along the rail, a pivot position of the sliding attachment ring relative to the rail, a linear position of the extended-reach device relative to the sliding attachment ring, and a rotational position of the extended-reach device relative to the sliding attachment ring.

19. The method of claim 18, further comprising accessing a database containing data pertaining to objects viewed by a camera included in the end effector; and displaying a stored image of one of the objects adjacent an actual image of the one of the objects viewed by the camera.

* * * * *